(12) United States Patent
Schellenberg

(10) Patent No.: US 9,445,721 B2
(45) Date of Patent: Sep. 20, 2016

(54) MR GAMMA HYBRID IMAGING SYSTEM

(76) Inventor: James Schellenberg, Winnipeg (CA)

( * ) Notice: Subject to any disclaimer, the term of this patent is extended or adjusted under 35 U.S.C. 154(b) by 112 days.

(21) Appl. No.: 13/576,995

(22) PCT Filed: Feb. 10, 2011

(86) PCT No.: PCT/CA2011/050074
§ 371 (c)(1),
(2), (4) Date: Oct. 1, 2012

(87) PCT Pub. No.: WO2011/097726
PCT Pub. Date: Aug. 18, 2011

(65) Prior Publication Data
US 2013/0137964 A1 May 30, 2013

Related U.S. Application Data

(60) Provisional application No. 61/303,137, filed on Feb. 10, 2010.

(51) Int. Cl.
| | |
|---|---|
| *A61B 5/055* | (2006.01) |
| *A61B 5/00* | (2006.01) |
| *A61B 6/04* | (2006.01) |
| *G01T 1/16* | (2006.01) |
| *A61B 6/03* | (2006.01) |
| *G01R 33/48* | (2006.01) |

(Continued)

(52) U.S. Cl.
CPC .......... *A61B 5/0035* (2013.01); *A61B 5/0555* (2013.01); *A61B 5/415* (2013.01); *A61B 5/418* (2013.01); *A61B 5/4312* (2013.01); *A61B 6/037* (2013.01); *A61B 6/0414* (2013.01); *A61B 6/0435* (2013.01); *A61B 6/40* (2013.01); *A61B 6/42* (2013.01); *A61B 6/4405* (2013.01); *A61B 6/4417* (2013.01); *A61B 6/502* (2013.01); *A61B 6/5247* (2013.01); *G01R 33/481* (2013.01); *G01T 1/1603* (2013.01); *A61B 6/107* (2013.01); *A61B 6/4488* (2013.01); *G01R 33/34046* (2013.01)

(58) Field of Classification Search
CPC ...................................................... A61B 5/055
USPC ........................................................ 600/411
See application file for complete search history.

(56) References Cited

U.S. PATENT DOCUMENTS

| | | | | |
|---|---|---|---|---|
| 6,946,841 | B2 * | 9/2005 | Rubashov | ...................... 324/318 |
| 7,402,813 | B2 * | 7/2008 | Ben-Haim et al. | ...... 250/370.09 |

(Continued)

FOREIGN PATENT DOCUMENTS

| | | |
|---|---|---|
| EP | 1356772 | 10/2003 |
| WO | WO 2009022270 A2 * | 2/2009 |

OTHER PUBLICATIONS

J-W Tan, L Cai, L-J Meng, "A Prototype of the MRI-Compatible Ultra-High Resolution SPECT for in Vivo Mice Brain Imaging", 2009, IEEE Nuclear Science Symposium Conference Record, pp. 2800-2805.*

*Primary Examiner* — Tse Chen
*Assistant Examiner* — Lisa Kinnard
(74) *Attorney, Agent, or Firm* — Ade & Company Inc.; Michael R. Williams

(57) ABSTRACT

A pendant breast imaging system that operates with a MRI system and which allows a planar gamma camera breast imaging system to be positioned away from the breast area while MRI imaging is occurring, and which then moves into breast imaging position after MRI imaging is complete, and which can again be removed from the breast area to allow intervention to occur is described. It may use various collimator or scintillator materials and designs.

20 Claims, 6 Drawing Sheets

(51) Int. Cl.
*A61B 6/10* (2006.01)
*A61B 6/00* (2006.01)
*G01R 33/34* (2006.01)

(56) References Cited

U.S. PATENT DOCUMENTS

| | | | |
|---|---|---|---|
| 2002/0143249 A1* | 10/2002 | Tornai et al. | 600/425 |
| 2003/0153830 A1* | 8/2003 | Weinberg et al. | 600/436 |
| 2007/0015987 A1* | 1/2007 | Benlloch Baviera et al. | 600/407 |
| 2007/0078329 A1 | 4/2007 | Vija | |
| 2008/0077005 A1* | 3/2008 | Piron et al. | 600/411 |
| 2008/0230704 A1 | 9/2008 | Daghighian | |
| 2009/0088627 A1* | 4/2009 | Piferi et al. | 600/422 |
| 2009/0156961 A1* | 6/2009 | Tsonton et al. | 600/562 |
| 2009/0209846 A1* | 8/2009 | Bammer | 600/421 |
| 2009/0270718 A1* | 10/2009 | Peter et al. | 600/411 |
| 2010/0016865 A1* | 1/2010 | Kieper et al. | 606/130 |

\* cited by examiner

MR GAMMA HYBRID IMAGING SYSTEM

PRIOR APPLICATION INFORMATION

The instant application claims the benefit of U.S. Provisional Patent Application 61/303,137, filed Feb. 10, 2010.

BACKGROUND OF THE INVENTION

There are two basic types of nuclear imaging systems for medical usage. Gamma imaging involves imaging one emission photon at a time, and collimators are usually part of the design. Positron imaging involves two emissions photons emitted in almost opposite directions, and collimators are not required as long as the detection system detects both photons. The invention of combined magnetic resonance imaging systems and nuclear medicine imaging systems began with U.S. Pat. No. 4,939,464 filed in 1989 by Hammer, which disclosed a combination NMR/PET scanner which uses light pipes to communicate the scintillation events to the exterior of the magnet. In this design, the detector could not be placed in the area of large magnetic fields because the materials and design used within the detector were adversely affected by magnetic fields, so light pipes connected the scintillator's optical output signals to the detectors which were outside the magnetic field area. The concept of using light guides and fiber optic connections between scintillator and detector have continued in other system designs, including U.S. Pat. No. 5,325,855 filed in 1992 in which the fibers offered flexibility of positioning for a surgeon, and U.S. Pat. No. 5,719,400 filed in 1995 and U.S. Pat. No. 7,835,782 filed in 2006 which uses optical fiber to allow positioning of the detectors outside of the magnetic field of the MRI system. An alternative design approach uses MR compatible PET detector systems that allow the detectors to be placed within the MR bore, and which then use detector output connection methods to connect the detector output to the outside world. This has been done in "MR Compatible PET Using Tileable GAPD Arrays", J H Jung et al, IEEE 2009 Nuclear Science Symposium Record, M13-27, pp. 3556-3559. These MR-PET hybrid systems are designed to allow simultaneous imaging to occur. Simultaneous imaging is achieved when the same region of space is imaged by both imaging methods at the same time. In order to achieve simultaneous imaging, the two imaging systems must be in imaging position at the same time, and must be designed to be compatible with each other.

PET systems are built for detecting two annihilation photons which are emitted in nearly opposite directions, with both photons being at an energy level of 511 keV. PET systems use two detecting heads at opposite sides of the volume under study, and they use electronic collimation instead of physical collimation. PET systems are designed to detect only 511 keV photons. Gamma detection systems, on the other hand, usually use a physical collimator because the energy is emitted only in a single direction. A collimator is built of a slab of heavy metal, typically lead, into which is drilled or fashioned a pattern of holes. The gamma rays can be emitted at energy levels ranging from 81 to 365 keV, depending on which compounds are injected into the patient. One common gamma camera front end design consists of collimator, scintillator, detector, and electronics, with the collimator excluding all gamma rays except those that line up with the openings in the collimator, the scintillator converting the gamma photon into an optical signal, the detector converting the optical signal to an electrical signal and the electronics conditioning that signal to allow further processing or display functions to occur. There has always been concern that introducing the metal collimator into the MRI bore during imaging would lead to imaging artifacts or other MRI image degradation. If the physical collimator is positioned between the RF coil and the patient, then the RF coil will not be able to image. Alternatively, if the RF coil is placed between the patient and the collimator, one must ensure that the RF coil does not alter the path or energy of the gamma photon. Positron emissions have a higher energy, and so are less affected by intervening materials. U.S. Pat. No. 7,394,254 discusses this issue, and provides an RF coil invention that is more transmissive of nuclear radiation.

Hybrid MR-Gamma imaging has been discussed within U.S. Pat. No. 7,629,586 which describes a ring-based gamma camera concept that is axially oriented with the bore of a superconducting MRI system. In this patent, the RF coil is closest to the patient, outside of which is the gamma camera, outside of which is then the gradient coil. The gradient coil is typically built into the bore of the MRI system. Usually, the RF Coil will be a receive only coil, with the transmit portion of the MRI imaging function being performed by the transmit coil which is built into the bore of the MRI system. In this invention, rotation of the camera about the bore axis is discussed. This design geometry is very close to the PET-MR design geometry, in which the superconducting bore axis is also the axis for a ring-based nuclear imaging camera. In this type of design, the collimator is kept away from the RF coil so that interference does not occur, and the distance from the patient to the camera is quite large. For human imaging, a typical MRI bore will be 70 cm in size, a typical gamma camera depth will be nominally 6 cm, and so the effective bore size in such a design is approximately 58 cm because the gamma camera in this design moves from one area of the bore to the other, thus requiring 6 cm to be reserved from both top and bottom of the bore. For existing smaller bore superconducting magnets of 60 cm nominal bore size, this gamma camera design leads to 48 cm effective bore size, which is restrictive for some bariatric patients. As well, for specific types of imaging positions and usages, such as human prone breast imaging, a hybrid MR-Gamma design such as this would have a gamma camera quite far from the breast, leading to a reduced sensitivity and accuracy. This type of design approach requires an RF coil which is gamma compatible. Additional work on a movable axially-oriented MR-Gamma hybrid system has been shown in "A Prototype of the MRI-Compatible Ultra-High Resolution SPECT for in Vivo Mice Brain Imaging", J-W Tan, L. Cai and L-J Meng, 2009 IEEE Nuclear Science Symposium Conference Record, pp. 2800-2805. In this paper, the SPECT system is moved in and out of the bore of the MRI on a non-magnetic gantry. Rotation about the bore axis is possible. In this design, the gamma camera is also outside the MRI RF receive coil. For an application such as human prone breast imaging, this design also suffers from having a gamma camera which may be quite distant from the breast area. As well, the RF coil that lies between the gamma camera and the patient needs to be gamma compatible. A thesis from London Ontario's Western University, by James William Kristian Odegaard (2007) entitled "Design and Performance Evaluation of a Small-Animal Pinhole-SPECT Array Insert for Field-Cycled MRI" discussed the organization of a SPECT camera as an insert into a field cycled MRI system. This insert is oriented along the axis of the MRI, and is not movable. This design also requires an RF coil that is gamma compatible. Previous work by Goetz et al ["SPECT Low-Field MRI System for Small Animal Imaging", C. Goetz et al, J. Nuc. Med Vol. 49 (1) January 2008 pp 88-93] has also shown non-simultaneous imaging in which a slab magnet is used. This paper discussed a bore aligned gamma camera which allows a small animal to be moved from the gamma camera area to the MRI imaging area along a common axis. It does not allow movement of the gamma camera into the magnetic field. The gamma camera and MRI bore are aligned.

Additional work on the development of fixed RF coil and gamma camera systems includes the designs of S. Ha et al, as shown in "Development of a new RF coil and γ-ray radiation shielding assembly for improved MR image quality in SPECT/MRI "*Phys Med Biol.* 2010 May 7; 55(9): 2495-504. Epub 2010 Apr. 6. In this case, holes were provided in the packaging of the RF coil, a specialized collimator mixture was used to form MR compatible collimator material that was inserted into these holes, and the gamma camera was positioned behind the holes and some distance from the RF coil.

Additional system design work is discussed in "Development of an MR-compatible SPECT system (MRSPECT) for simultaneous data acquisition", Mark J Hamamura, Seunghoon Ha, Werner W Roeck, L Tugan Muftuler, Douglas J Wagenaar, Dirk Meier, Bradley E Patt and Orhan Nalcioglu, Published 17 Feb. 2010, Phys. Med. Biol. 55 (2010) 1563-1575. As the title indicates, this design is for simultaneous imaging, which requires that both gamma and MR system be in imaging position at the same time, which therefore requires that MR and gamma compatibility is required of the various system elements. Most importantly, in this design the RF coil is of a birdcage variety, and the collimator is moved directly through the rungs of the birdcage coil. The sample can be rotated to allow SPECT imaging. In this case, the effect of the collimator on the MR imaging is shown to cause changes to RF coil loading, and so adjustment of the coil trim capacitors is required. This design only allows for insertion of the collimator through the rungs, and so the depth of the collimator must be sufficient to extend from the back side of the RF coil packaging to the imaging position that the application requires. In this design, the collimator is inserted directly through the rungs of the birdcage coil, and so the separation of the rungs dictates the width of the collimator. The sample to be imaged, however, might be larger than the width of the rungs. For example, for breast or brain imaging in which an RF birdcage coil is used, the specific area to be imaged may be of larger size than the width between the rungs. In the case of breast cancer, the breast is typically of size 11 cm width with a pendant length of 10 to 15 cm, so the birdcage rung width would need to be very large to accommodate so large a collimator. Commercially available birdcage coils do not have such large rung spacings. Also, the area to be imaged may not be directly behind the area outlined by the rungs, and so the sample must be rotated to allow the desired area to be imaged more closely. For human breast or brain imaging, and indeed for many human and animal imaging situations, including diagnostic, interventional and intra-operative imaging applications, it is not possible nor permissible to rotate the patient. In human medical imaging applications it may also not be possible to rotate the coil. For example, for brain imaging during brain surgery, the lower part of the head coil is usually fixed in place throughout the operation, and so rotation is not allowed. Importantly, for this design to operate in simultaneous imaging mode, they discuss the alteration of the RF Coil trim capacitors based on amount of collimator insertion that occurs. Altering RF Coil trim capacitors is not allowed on most commercially available RF coils, and so this type of design may be required to have a customized coil design.

An additional application of interest is US 20100264918 invented by Roeck and Nalcioglu in which is disclosed a unique motor design for rotating a specimen that can be simultaneously imaged by SPECT and MRI methods. They use the same figures for RF birdcage coil and collimator orientation as are used in the paper above, and are authors of the above paper as well. In this design, the animal being imaged is rotated about the bore axis of the magnet. They indicate that they can improve post-processing of the SPECT image using MRI data, however they do not discuss changing the position or orientation of their collimator based on MRI data. In this invention, there is no concept of altering the orientation of the collimator, but there is the concept of moving the collimator closer to the sample or further away from the sample. This design also uses a collimator which is the same width as the width between the rungs of the birdcage. This design also uses a custom designed bird-cage coil. This invention does not discuss the alteration of the capacitors based on the depth of insertion of the collimator, but we assume that simultaneous imaging and optimal operation of the RF coil would require such a capacitor adjustment.

To summarize, the previous work has shown a few MR gamma hybrid system designs that are focused on simultaneous imaging of the sample, with these systems not being optimized for some medical applications such as human breast imaging in the prone position using commercially available RF coils. These existing designs require gamma compatible or specialized RF coils, and are not designed to interwork with existing commercially available RF breast coils. The one non-simultaneous hybrid system moved the sample between the MRI and nuclear imaging positions.

There are various designs for RF coils. A typical head-imaging coil uses a birdcage design which has openings to allow access and visibility. This type of coil design for the head is provided by various companies, with a particular focus on allowing sufficient room between the coil and head to allow other instruments to be introduced if intra-operative and interventional applications need to be performed. As well, it is necessary to allow visibility for the patient in those cases where an awake patient is being imaged.

For breast imaging similar types of coil designs have been discussed within US Patent Application 2009/0118611. In this design, a butterfly tape RF coil design is suggested which will cause the inner surface of the RF coil to be some distance from the breast being imaged. Also for breast imaging, coils may be built into the upper body surface or lower table surface to allow for ease of access for breast biopsy, therapy, ablation or needle and marker placement.

For brain and breast imaging and for imaging other body parts that have an RF coil some distance from the body, if hybrid MR-gamma imaging is desired, it would be useful to have an imaging method, system and device that allows the gamma camera to be positioned close to the patient. Allowing the gamma camera to image close to the patient will improve imaging specificity, sensitivity, reduce patient dosage levels and improve spatial resolution of the imaging. It will also allow more flexibility in the materials used for RF coil and gamma camera, leading to increased product availability and lower cost. It may also allow the gamma camera to be used in retrofit fashion with existing RF coils. The previous designs are limited because the collimator width is the same as the birdcage rung width. A different insertion method might allow better imaging for some applications. It may also be useful in some applications to have a gamma camera that can be inserted and removed from the patient area to allow optimum patient access for follow-on procedures such as biopsy, ablation, therapy and needle or guide insertion if necessary for interventional and intra-operative procedures. The previous designs have not indicated any method whereby they could be removed for interventional tool or device access. It may also be useful to have a removable gamma camera so that sterilization of the gamma camera packaging is not required. For example, some procedures and workflows would have a surgeon accessing the breast or brain area through the MRI coil using surgical instruments, and so if the gamma camera remains in place it would need to have more stringent sterilization procedures than a design that did not cause the gamma camera to remain in place. It may also be useful to have a gamma camera that can take on different orientations or spatial distances depending on the size of the body part, such as a breast, that is being imaged. Breasts vary in size from one patient to the next, and the suspected tumor location may change the optimum position for the gamma camera. As well, for brain surgical interventions the head may be positioned differently within the RF coil. As well, for small gamma cameras that are used for lymph node imaging, there may be restricted access to the breast tail and underarm area. It would also be useful to have a gamma camera that can be moved within the RF coil volume so that different types of RF coils, or different sizes of RF coils, may be used with a single gamma camera design. It may also be useful to have a movable gamma camera because different radioisotopes may be best imaged from different directions or distances. It would also be useful to have a gamma camera that can be inserted and removed from the RF coil so that the gamma camera can also serve in situations where MR systems are not used. For example, it is possible that a patient cannot be imaged in the MRI system due to claustrophobia issues or because the patient has metal items inside the body, but that a scinti-mammography session would still be useful for the patient, and so with a removable gamma camera system it is possible to also use the gamma camera for non-MRI based situations and applications, including breast screening, breast diagnostic imaging, breast biopsy imaging and guidance, bone scintigraphy, breast neo-adjuvant therapy monitoring, and other uses that are known in the art. If the RF coil and gamma camera are built together or fixed together in some way, then additional and multiple applications may not be possible. If the coil and camera systems are built together in some way, then replacement of equipment elements may become more complex and more costly. In addition, it would be useful to have a gamma camera architecture and design that is useful for both superconducting bore MRI systems as well as slab systems, for both vertical field and horizontal field applications.

The geometries and designs described herein offer improved usages for some medical imaging applications.

SUMMARY OF THE INVENTION

According to an aspect of the invention, there is provided a magnetic resonance imaging (MRI) compatible gamma camera comprising:
an MRI-compatible gamma camera head arranged to be inserted through an opening in a MRI coil;
a gamma shield; and
a non-MRI compatible processing system connected to the gamma camera head by cabling.

According to another aspect of the invention, there is provided a pendant breast imaging system comprising:
a table for a patient to rest thereon, said table having a raised platform with openings for the face and breasts of the patient;
a bore based or slab based magnetic resonance imaging (MRI) system having a radiofrequency (RF) coil, said RF coil having an opening therein; and
a magnetic resonance imaging (MRI) compatible gamma camera comprising:
an MRI-compatible gamma camera head arranged to be inserted through the opening in said RF coil;
a gamma shield; and
a non-MRI compatible processing system connected to the gamma camera head by cabling.

According to a third aspect of the invention, there is provided a method of imaging a breast comprising:
providing a patient lying on a table, said table having a raised platform with openings for the face and breasts of the patient;
providing a bore based or slab based magnetic resonance imaging (MRI) system having a radiofrequency (RF) coil, said RF coil having an opening therein;
generating an MRI image of the breast of interest by placing the RF coil proximal to the breast of interest;
providing a magnetic resonance imaging (MRI) compatible gamma camera comprising:
an MRI-compatible gamma camera head arranged to be inserted through the opening in said RF coil;
a gamma shield; and
a non-MRI compatible processing system connected to the gamma camera head by cabling;
inserting the gamma camera head through the opening in the RF coil such that the gamma camera head is closer to the breast of interest than the inner diameter of the RF coil; and
generating a gamma image of the breast of interest, characterized in that the magnetic resonance imaging and the gamma imaging are carried out sequentially and the patient is not moved or repositioned during the imaging process.

DETAILED DESCRIPTION OF THE PREFERRED EMBODIMENTS

Figure 1:
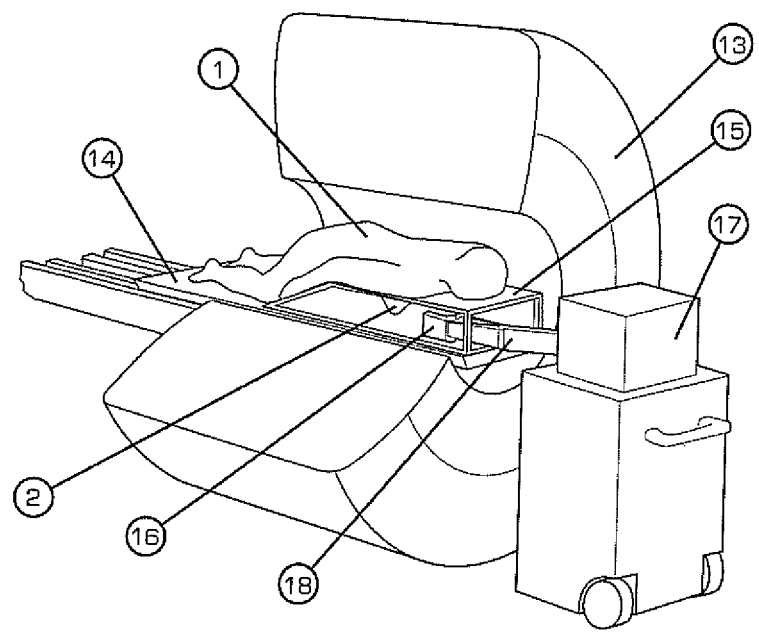
FIG. 1—Bore-Based In-Field MRI-Gamma Hybrid Breast Imaging System.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As discussed herein, there is provided a magnetic resonance imaging (MRI) compatible gamma camera comprising: an MRI-compatible gamma camera head arranged to be inserted through an opening in a MRI coil; a gamma shield; and a non-MRI compatible processing system connected to the gamma camera head by cabling.

The gamma camera head may comprise a collimator, a scintillator, a detector and an electronics assembly.

The gamma camera head may be substantially planar.

The gamma camera head may be connected to an articulated arm for positioning the gamma camera head.

In another aspect of the invention, there is provided a pendant breast imaging system comprising: a table for a patient to rest thereon, said table having a raised platform with openings for the face and breasts of the patient; a bore based or slab based magnetic resonance imaging (MRI) system having a radiofrequency (RF) coil, said RF coil having an opening therein; and a magnetic resonance imaging (MRI) compatible gamma camera comprising: an MRI-compatible gamma camera head arranged to be inserted through the opening in said RF coil; a gamma shield; and a non-MRI compatible processing system connected to the gamma camera head by cabling.

The pendant breast imaging system may further comprise a breast paddle for holding a patient's breast during imaging.

The gamma camera head may include alignment protrusions for aligning the gamma camera head onto the breast paddle.

The gamma camera head may be arranged to be inserted through the opening in the RF coil such that the gamma camera head is closer to the patient than the inner diameter of the RF coil. The opening in the RF coil is a slot in the RF coil or may be formed by removing a portion of the RF coil or by deforming the RF coil.

In another aspect of the invention, there is provided a method of imaging a breast comprising: providing a patient lying on a table, said table having a raised platform with openings for the face and breasts of the patient; providing a bore based or slab based magnetic resonance imaging (MRI) system having a radiofrequency (RF) coil, said RF coil having an opening therein; generating an MRI image of the breast of interest by placing the RF coil proximal to the breast of interest; providing a magnetic resonance imaging (MRI) compatible gamma camera comprising: an MRI-compatible gamma camera head arranged to be inserted through the opening in said RF coil; a gamma shield; and a non-MRI compatible processing system connected to the gamma camera head by cabling; inserting the gamma camera head through the opening in the RF coil such that the gamma camera head is closer to the breast of interest than the inner diameter of the RF coil; and generating a gamma image of the breast of interest, characterized in that the magnetic resonance imaging and the gamma imaging are carried out sequentially and the patient is not moved or repositioned during the imaging process.

The positioning of the gamma camera may be determined by the results of the magnetic resonance imaging. Specifically, the gamma camera may be positioned optimally to more closely examine lesions or potential lesions identified in the magnetic resonance image. As will be appreciated by one of skill in the art, the fact that the MR imaging and gamma imaging are carried out sequentially without the patient being moved or repositioned facilitates this process. That is, the imaging is done sequentially, not simultaneously as discussed herein. The system and method are further improved in that the breast paddle that holds the breast during MR analysis is not moved during gamma imaging and in fact the gamma camera described herein is arranged to be mounted onto the breast paddle as discussed herein.

As discussed herein, the gamma camera system is arranged to be moved from a first position outside of the fringe field of the MR system to a second position in which the MR compatible gamma camera head is inserted through an opening in the RF coil to a position that is closer to the patient's breast than the inner diameter of the RF coil for gamma imaging. It is of note that as discussed herein, the gamma camera head may be moved by means of an articulated arm. It is further noted that the gamma camera head may be moved to a third position outside of the RF coil or back to the first position to provide access for the surgeon or physician or technician, as discussed in greater detail below.

The magnetic resonance image and the gamma image may be co-registered.

According to a first aspect of the invention, there is provided a pendant breast imaging system that operates with a MRI system, and which allows a planar gamma camera breast imaging system to be positioned away from the breast area while MRI imaging is occurring, and which then moves into breast imaging position after MRI imaging is complete, and which can again be removed from the breast area to allow intervention to occur. It may use various collimator or scintillator or detector materials and designs. It may use CZT direct detection or some other material for direct detection or it may use silicon photomultiplier or APD (Avalanche Photodetector) technology which is MR compatible.

This invention is an MR compatible gamma camera system that comprises a distal gamma camera head, a gamma shield, a proximal processing system, and an interconnection between the head and processing system.

The proximal processing system consists of data processing systems to transform the distal head signals into DICOM compatible images. The processing system also may receive status information from the distal head, and may also provide control signaling to the distal head.

The interconnection consists of cabling for power, control and data signals, and may also include cooling air supply. The data signal and control cabling will go directly through the filter panel of the MR room in some situations. The data signaling will be sent to the processing system from the gamma camera head. The electronic control signals, if present, will come from the processing system. The power and cooling air supply may be supplied via equipment booms or panels that are provided within the MR room. The interconnection system may also include an articulated arm or movement system, depending on the particular scenario for usage. In some situations, it is most suitable for the attending nurse or physician to pick up the distal head and place it by hand. The head shield, if required, will be placed on the opposite side of the breast and on the other side of the breast paddle. This head shield will be made of lead or other suitable material and will be placed by hand as well in some cases.

The distal head is a package with connectorization inputs and outputs. The package is between 5 cm×5 cm and 13 cm×13 cm, the size of the $90^{th}$ percentile breast, and is typically between 2 and 6 cm in depth. The package does not need to be square in shape. Inside the package is a mechanical assembly, on which is mounted a collimator, scintillator, detector and electronics assembly. Cabling connects the electronics assembly to the connector and then on to the interconnection cabling. Cooling air input and output sections, if required, are provided on the exterior of the package. The power dissipation of the distal head will range from typically 5 W or less to 20 W depending on the specifics of the design, such as size of the detector area, technology used for the detectors, and methods of interconnection which is used. The collimator, scintillator and detector (csd) are located on a mechanical assembly that can be controlled to allow the csd to take up a more optimum position for imaging, with the more optimum position being decided either by the human operator based on the results of the MRI imaging session that has just been concluded, or by an algorithm within the proximal processing system that outputs control signals to the mechanical assembly within the distal head package. The exterior packaging of the distal head will include alignment guides. These two or more alignment guides can be inserted into the two or more fenestrations of the breast paddles. Different breast paddles have different fenestration shapes and different breast holding methods, and so the detailed design of the external packaging of the distal head is customized depending on the specific breast paddle supplier that is being used.

Unlike previous designs, this invention provides a hybrid MR-gamma system that allows the planar gamma camera to be placed as close as possible to the human breast for breast cancer imaging, and which allows the planar gamma camera to be flexibly positioned inside or between the RF coils, and which allows the collimator position to be adjusted based on the MRI session results. This system is useful in both horizontal and vertical field applications because the coil and gamma camera are separate parts. In those cases where birdcage RF coils are used, the size of the planar gamma camera collimator can be wider than the birdcage rung width, and this is achieved by inserting the collimator, scintillator and detector through the rung at a sideways angle. Using this approach, various sizes of samples may be imaged through a relatively small birdcage coil slot. For example, breasts are typically 11 cm in diameter, but will become larger in one direction and smaller in the other when the breast paddles are applied. For example, an 11 cm diameter breast may become 8 cm in one direction and 14 cm in the other direction once the breast paddles are used to lightly compress the breast. As well, it is useful to gamma image through the shortest amount of tissue, and so the gamma camera collimator width for a parallel hole collimator can be 13 cm or more depending on the design of the system. Our design allows a 13 cm wide collimator to be inserted through a much narrower birdcage slot if the angles involved are suitable.

Another advantage of our method is that the breast paddles can be used as alignment and support guides, in order to make the mechanical design as easy as possible for the gamma camera system. This is intended to reduce the cost as much as possible.

Another advantage of our method is that the MR imaging information can be used to modify the orientation of the collimator-scintillator-detector assembly. For breast imaging, it is known that MRI imaging is highly sensitive. This implies that nearly all of the possible lesion locations are known in advance before gamma imaging occurs. For this reason, performing MRI imaging first, followed by gamma imaging, allows the gamma imaging system consisting of collimator—scintillator—and detector to be more optimally oriented.

Our design is not intended for simultaneous imaging, and so no adjustment of the capacitors within the RF coil is required.

A further advantage of this type of design is that the RF coil and the gamma camera are not integrated, which allows for easier retrofit, repair and upgrade of the two pieces. If the pieces are integrated in some way, then cost of the retrofit, repair and upgrade will probably be increased as well.

For brain and breast imaging and for imaging other body parts that have an RF coil some distance from the body, if hybrid MR-gamma imaging is desired, it would be useful to have an imaging method that allows the gamma camera to be positioned closer to the patient and inside the RF receive coil. Allowing the gamma camera to image close to the patient will improve imaging specificity, sensitivity, reduce patient dosage levels and improve spatial resolution of the imaging. It will also allow more flexibility in the materials used for RF coil and gamma camera, leading to increased product availability and lower cost. It may also allow the gamma camera to be used in retrofit fashion with existing RF coils. The previous designs are limited because the collimator width is the same as the birdcage rung width. A different insertion method might allow better imaging for some applications. It may also be useful in some applications to have a gamma camera that can be inserted and removed from the patient area to allow optimum patient access for follow-on procedures such as biopsy, ablation, therapy and needle or guide insertion if necessary for interventional and intra-operative procedures. The previous designs have not indicated any method whereby they could be removed for interventional tool or device access. It may also be useful to have a removable gamma camera so that sterilization of the gamma camera packaging is not required. For example, some procedures and workflows would have a surgeon accessing the breast or brain area through the MRI coil using surgical instruments, and so if the gamma camera remains in place it would need to have more stringent sterilization procedures. It may also be useful to have a gamma camera that can take on different orientations or spatial distances depending on the size of the body part, such as a breast, that is being imaged. Breasts vary in size from one patient to the next, and the suspected tumor location may change the optimum position for the gamma camera. As well, for brain surgical interventions the head may be positioned differently within the RF coil. As well, for small gamma cameras that are used for lymph node imaging, there may be restricted access to the breast tail and underarm area. It would also be useful to have a gamma camera that can be moved within the RF coil volume so that different types of RF coils, or different sizes of RF coils, may be used with a single gamma camera design. It may also be useful to have a movable gamma camera because different radioisotopes may be best imaged from different directions or distances. It would also be useful to have a gamma camera that can be inserted and removed from the RF coil so that the gamma camera can also serve in situations where MR systems are not used. For example, it is possible that a patient cannot be imaged in the MRI system due to claustrophobia issues or because the patient has metal items inside the body, but that a scinti-mammography session would still be useful for the patient, and so with a removable gamma camera system it is possible to also use the gamma camera for non-MRI based situations and applications, including breast screening, breast diagnostic imaging, breast biopsy imaging and guidance, bone scintigraphy, breast neo-adjuvant therapy monitoring, and other uses that are known in the art. If the RF coil and gamma camera are built together or fixed together in some way, then additional and multiple applications may not be possible. If the coil and camera systems are built together in some way, then replacement of equipment elements may become more complex and more costly. In addition, it would be useful to have a gamma camera architecture and design that is useful for both superconducting bore MRI systems as well as slab systems, for both vertical field and horizontal field applications.

According to a further aspect of this invention, any of the above systems may have an MR system that is also movable, such as in the manner of IMRIS. The IMRIS system completely moves the superconducting MRI bore away from the patient. The IMRIS MRI inventions are described in U.S. Pat. No. 5,735,278 and published US Patent Applications 2008/0039712 and 2009/0124884.

In all of these designs, the breast must be held using breast paddles, as is commonly available for these types of systems. In all of these designs, the patient and breast do not move, thereby allowing co-registration methods using fiducials to be used to register the MR and gamma image. In all of these designs, it is possible to improve gamma imaging by using the knowledge already gained from the MRI imaging session that is done immediately before the gamma image. In all of these designs, the MR image is performed first, followed by the gamma imaging, followed by co-registration and analysis. Mounting the gamma camera onto the breast paddle is unique to this design. Using this approach may allow very simple alignment methods to be used for gamma camera imaging of suspected lesions.

Therefore, the invented apparatus is a movable gamma camera and associated mounting hardware optimized to interwork with a movable or static RF coil, a movable or static patient bed, and a movable or static MRI Magnet system, with any combination of these imaging subsystems movable, all being moved or remaining static without causing the patient to change her position relative to the table between the MRI and gamma imaging sessions.

In some embodiments, there is provided a superconducting bore-based MRI system in which an articulated arm is used to insert a gamma camera into a breast imaging space by inserting the gamma camera through openings in the RF coil packaging so that the gamma camera is able to image from distance closer than the inner diameter of the RF receive coil. This same approach can also be used to insert a gamma camera through the openings of an RF coil used for head and upper spinal cord imaging to allow the gamma camera to be used closer to the patient's body surface or to allow the gamma camera to be inserted into the patient's surgical cavity or opening. It is understood that the RF coil could be a receive/transmit or receive variety. It is understood that this insertion and removal may occur in the bore of the MR system, in the fringe field, or at a distance removed from the bore and fringe field but with at least a portion of the RF coil still in position about the body part, whether breast, brain or other part.

There is also described herein a slab MRI system in which an articulated arm is used to insert a gamma camera into a breast imaging space by inserting the gamma camera through openings in the RF coil packaging so that the gamma camera is able to image from a distance closer than the inner diameter of the RF coil.

There is also described herein a movable gamma camera, which is inserted into the breast imaging area by being inserted through an opening in the MRI coil.

There is also described herein a movable gamma camera which is inserted into the breast imaging area after the MRI coil is partially or fully removed Also described is a movable gamma camera which is inserted into the breast imaging area after MR imaging, and which is not oriented along a horizontal axis of the room, but is instead oriented along the vertical axis that is characteristic of the pendant breast that is being imaged.

Also envisioned is a movable gamma camera which is inserted through openings in the MRI coil, and which uses the paddles for support and guidance while being positioned, and which paddles have fiducials that allow registration of the resulting mri and gamma images.

This two-piece gamma camera allows easier integration with other MR compatible equipment such as MRI coil, biopsy systems and ablation tools, in that the front head can be made relatively small and less expensive, and because the connection between the front head and back section can be made easily removable, so that the positioning of the MRI coil with gamma front head can be done first without the interconnection being present, followed by a future interconnection of the front head to the back section by the interconnection being pushed into the front section. It is understood that the cabling between front head and back section may require cable traps or heat dissipation methods, and it is understood that this system can be used both for in-bore systems (both high field and low field) and not-in-bore systems (for both high field and low field MRI systems).

It is understood that the separable gamma camera with an MR compatible front section may allow the front section to remain in place in a non-imaging position during the MRI imaging process, after which the rear section electronics can be connected to the gamma camera This separable gamma camera can be used for easy positioning through the slots of the MRI coil and will allow easier design and development of the MRI coil. It is also possible that the separable gamma camera will allow easier retrofit to existing MRI breast coils.

It is understood that the exact position of the gamma camera may be determined by the findings of the MRI imaging session. That is, if the MRI imaging session with its high sensitivity finds a specific number and geometric orientation of potentially cancerous lesions, it is possible to position the gamma camera in such a way that the gamma camera heads can optimally detect the potentially cancerous lesions.

In general, a Movable Gamma camera system used with MRI that has the following features:
  the gamma camera is used with an RF coil system that has openings, such that the gamma camera can be inserted through the openings of the coil to allow gamma imaging to occur;
  the position of the gamma camera is adjusted based on the MRI imaging, because MRI imaging with very high sensitivity implies that all lesions of interest will be seen using MRI, and so gamma is used for specificity improvement:
  or (a second method of positioning) that the gamma camera is separable after the detector section, that it consists of a gamma camera head, cabling, and a processing system that is operating in the background, potentially in the internet somewhere for lowest cost, allowing the smallest possible item to be placed near the breast area;

that the gamma camera physical location is determined by aligning the gamma camera with the fenestrated breast paddle holes by having suitable physical bumps or alignment protrusions on the gamma camera front face, with these bumps or protrusions being specific for the particular paddle that is being used;

that the gamma camera distal portion is connected via cabling through the filter plate of the MRI room to the processing system inside the control room, and that the processing system may be completely implemented in software;

that there are two gamma camera sections that can be used, one for each breast, and that they are placed as appropriate for each breast.

that co-registration is used to align the MRI and gamma images so that they are most useful for the attending medical staff.

FIG. 1 illustrates in a cut-away view a female patient 1 lying face down (prone) in the pendant breast position, with her breast 2 pendant through an opening of the upper body support system 15, on an MR compatible table 14, within a superconducting 1.5 T, 3 T or other field strength superconducting MRI system 13, with a gamma camera system 16 being moved towards the breast imaging position using the articulated arm 18. The gamma camera positioning and image processing system 17 allows for gamma camera equipment positioning within the bore of the MRI system. Not shown in this diagram is the RF coil and breast paddle. For existing products, the RF coil may be built into the upper and lower parts of the upper body support system, and are therefore not visible. In other existing designs, the RF coil may be built into the breast paddle itself. In other existing designs, the RF coil may be removable.

For this system, two workflows are possible, depending on when the radiopharmaceutical is injected. One workflow is first to inject the patient with suitable radiopharmaceuticals, then to initiate MRI imaging (either with or without gadolinium contrast agent as required by the MRI sequence), then to initiate gamma imaging by inserting the gamma camera through an opening in the RF coil packaging, then to hold the gamma camera in imaging position to allow the imaging to occur, and to then remove the gamma camera from the RF coil volume. Alternatively, it is possible to wait until after MR imaging before introducing the radiopharmaceutical to the patient.

In the particular example drawn here, the patient is inserted head first into the bore of the MRI system and the gamma camera system is inserted from the opposite end of the MRI bore. Three other in-bore geometries exist, which are:

(2) patient feet first into bore, gamma camera arm comes in from opposite end (3) patient head first into bore, gamma camera arm comes in from same end (4) patient feet first into bore, gamma camera arm comes in from same end.

The decision of the particular geometry to use is not straightforward because in the event that in-bore biopsy, surgical access, or ablation is being considered, the size and movements of the biopsy, surgical or ablation systems might partially dictate the direction and access volumes for the gamma camera. In all cases, however, the gamma camera is inserted into the bore and is moved to a position closer to the patient than the RF coil inner diameter.

In each of the four geometries, the size of the articulated arm 18 dictates whether the gamma camera positioning and image processing system 17 needs to be fully MR compatible or not. If the arm 18 is long enough and if the fringe field does not extend too far, then the processing system 17 might be moved outside of the fringe field area. The length required for such an articulated arm will vary depending on the length of the bore, the positioning of the patient, the MR compatibility of the processing system, and the weight of the gamma camera head. This type of design is useful in those cases where the patient is not moved between imaging sessions, and in which the patient must be imaged in-field.

In all cases, it is understood that the MR and gamma images that are obtained may be co-registered with each other to allow improved imaging resolution or analysis. This co-registration process may involve the placement of fiducials on the female breast or on the breast paddles using methods that are commonly known.

It is also understood that both MR imaging and gamma imaging can be performed on one or both breasts at the same time. In the case of two breast imaging, both breasts are pendant, two articulated arms can be used, each one with a gamma camera head at its end, and positioning of the two gamma camera heads can be done separately.

Figure 2:
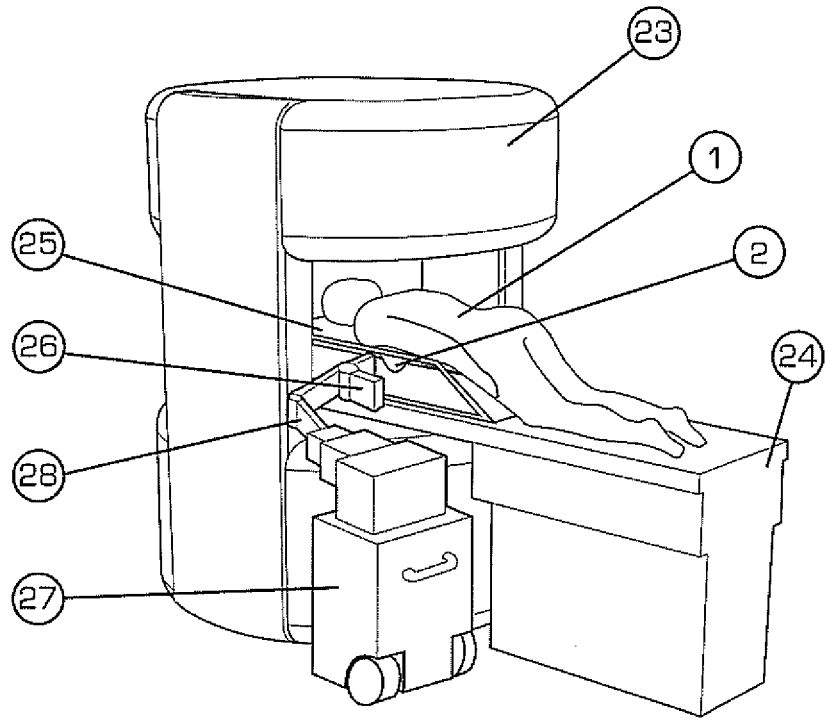
FIG. 2—Slab-Based in-Field MRI-Gamma Breast Imaging System.

FIG. 2 illustrates a female patient 1 lying face down in the pendant breast position, with her breast 2 pendant through an opening of the upper body support system 25, on an MR compatible table 24, within a slab based MRI system 23 that is typically of field strength 0.1 T, 0.3 T, 0.6 T, 1.2 T or magnet field strengths between these values, with a gamma camera head 26 being moved towards the breast imaging position using an articulated arm 28, and with the gamma camera processing system 27 being connected to the gamma camera head using cabling for information transfer and articulated arm for mechanical support.

In this slab-based design, the gamma camera system can be positioned to enter into the patient area from the side of the MRI or from the top of the MRI (top being at the patient's head), allowing greater flexibility in the positioning of the imaging elements. In addition, the slab-based system operating at magnetic field strengths typically below 0.6 T to 1.2 T with a vertical field will have a fringe field that is much closer to the MRI system, so the system 8 may not need to be MR compatible. In this situation, the length of the articulated arm will probably not have to be as long.

It is understood that along with the articulated arm will be control, status, power and data cabling that is suitable for the detector system being used.

FIG. 2 again shows a situation in which the patient remains in a single position in-bore, and the gamma camera is brought into position after MR imaging. Two workflows are possible with this system, with the radiopharmaceutical being delivered to the patient either prior to the start of MRI imaging or after completion of the MRI imaging.

In the case of both breasts being imaged by the gamma system, if the gamma camera is introduced from the side of the patient, a separate cable would be used to connect the second breast's camera head to the processing system. In the case where there is sufficient access near the top of the patient for the introduction of two articulated arms, then a single processing system can be used with two articulated arms and two gamma camera heads. In all cases, if shielding on the opposite side of the breast is required, a third and potentially a fourth articulated arm would be required to hold the shielding in place. Alternatively, the shield and camera head for a given breast can be controlled by the same articulated arm. In all cases, the breasts are held in place by breast paddles. The breast paddles are not shown on the figure.

Alternative equipment geometries are possible if the patient is moved after the MRI imaging. The workflow in this case would be for the patient to receive radiopharmaceutical injection, for the patient to be positioned on the table and then moved into the MR bore, for MRI imaging to occur, for the patient to be removed from the bore but still in the imaging position with the breast unmoved relative to the table, after which the gamma camera is brought to a position closer than the inner diameter of the RF coil, for gamma imaging to be done, and the gamma camera is then removed from the area close to the breast. For example, if the RF coils being used are of the variety available from NORAS, the patient can be inserted and removed from the MRI bore and a portion of the RF coil can be removed from the breast area, after which a gamma camera of suitable size and design could be moved close to the breast within the volume of the RF coil inner diameter, imaging could occur, and then the gamma camera could be moved away, all using existing RF coil and breast paddles. In this case, the gamma camera would have to be suitably sized and designed to retrofit to these existing designs.

For bore based MRI systems, the fringe field is of high magnetic field strength and extends out of the bore. For slab MRI systems, some of these fringe field effects are reduced.

Figure 3:
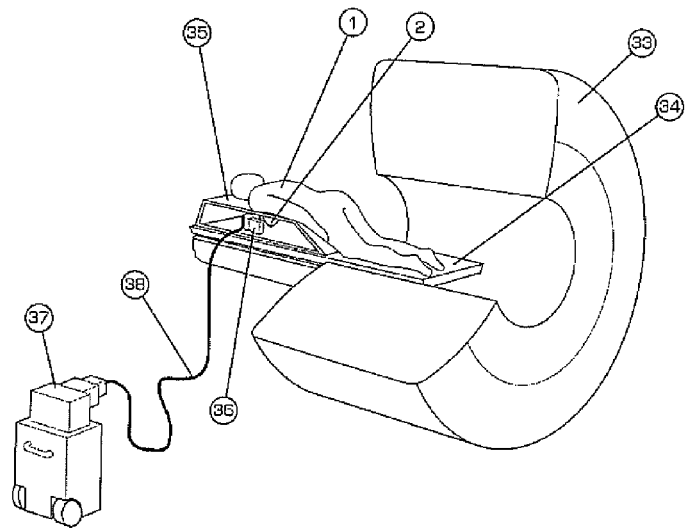
FIG. 3—Bore-Based MRI-Gamma Hybrid Breast Imaging System with Patient out of the Bore, Feet First Imaging (It is assumed that the system is still in the 5G field range).

FIG. 3 shows a Bore-Based MRI-Gamma Hybrid Breast Imaging System with Patient out of the Bore, Feet First Imaging. This figure is typical of MRI breast imaging orientations currently used by some companies, in which the patient 1 is first positioned on the table 34 and upper body support 35, the pendant breast 2 is then positioned with the positioning including stabilizing the breast 2 position with the use of fenestrated breast paddles (not shown), then the patient is inserted into the MRI 33 for MRI imaging, and then the patient is removed from the MRI. We then attach a gamma camera head 36 onto the fenestrated breast paddle (not shown) and then connect the processing system 37 to the gamma camera head using connector 38, after which gamma imaging is performed for approximately 5 to 10 minutes, after which the connector 38 can be disconnected and removed from the area, the gamma head 36 can be removed from the fenestrated breast paddle (not shown), and the image results can be compared and/or co-registered so that biopsy, therapy, or marker placement can be done. No articulated arm is required in this case because mechanical support is not required.

This patient position, in which the patient is out of the bore for gamma imaging, allows for an improvement in human access to the breast 2 area, and allows the nurse and/or practitioner to position the gamma camera head 36 onto the breast paddle (not shown) by hand, thereby saving cost and complexity as opposed to using an articulated arm. That is, even though an articulated arm is shown in the Figure, it is understood that cabling is always required even if the articulated arm is present. If the articulated arm is not required for mechanical reasons or for positioning reasons, then only the cabling is left as the interconnection between the camera head and the processing system. As well, positioning the gamma camera head 36 on the fenestrated breast paddle assists with the orientation of the gamma camera head, and allows some measure of mechanical support for the gamma camera head position. There are various designs for the fenestrated breast paddle from various manufacturers, and so the connection method of the gamma camera head will be slightly different for different systems.

This system configuration is also different from the previous two configurations because the system is able to operate in the fringe field of the superconducting bore, and so the magnetic field strength will be reduced. As well, in those cases where a portion of the RF coil is removed, this removal can be done prior to the gamma camera being positioned. For example, Noras (Germany) has a 4 channel breast coil and biopsy system available commercially in which 2 channels can be removed. This allows an increase in the accessible space for intervention, and will also allow an increase in accessible space for gamma imaging.

After the gamma images are obtained, they are fused with the MR images to make a set of images that are co-registered.

Figure 4:
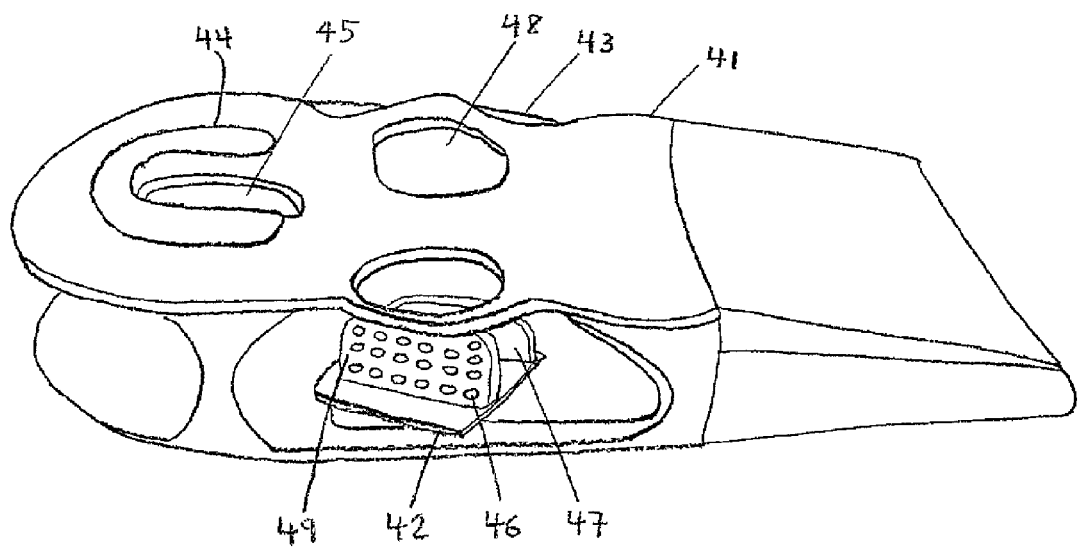
FIG. 4—Upper body support with breast paddle system.

FIG. 4 illustrates one example of commercially available upper body support 41 with breast paddle system 42. This breast paddle system 42 consists of the lower plate, on which is attached a movable fenestrated front breast paddle 49 which pushes the breast against the rear breast paddle 47, and nominally causes the breast to have a thickness of 11 to 5 cm, depending on breast size, patient care and comfort, and requirements for the intervention. The fenestrations 46 could be circular, squarish or hexagonal. Sometimes horizontal rungs or rods are used instead of fenestrations. In this example the left breast is under inspection, and the right breast hole 48 is covered by an insertible element 43 that blocks the right breast from falling through the hole. The upper body support has a headrest 44 and a breathing and access space 45 for the patient's face. This type of device is commercially available in the marketplace from a variety of vendors, with variations in the design depending on the manufacturer. The breast paddles system 42 in this example can be rotated about the vertical axis, allowing access to the breast from various directions for interventional work.

Figure 5:
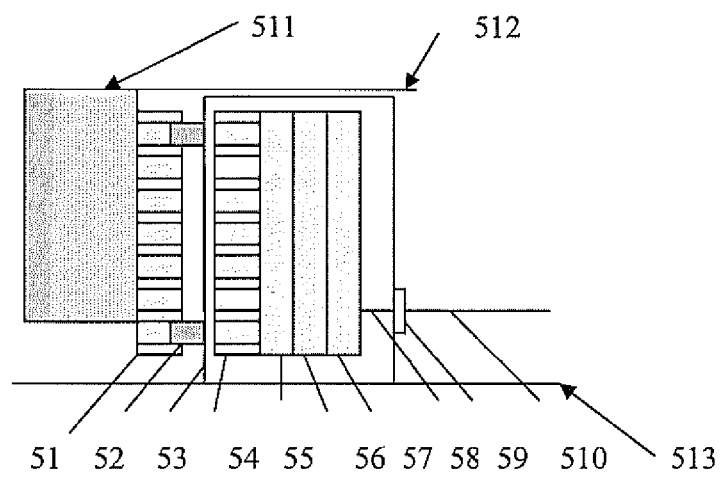
FIG. 5—Planar Gamma Camera Head with Breast Paddle.

FIG. 5 shows a side view of the arrangement of a planar gamma camera head and the fenestrated front breast paddle. In the case where the articulated arm is not used for mechanical support, the gamma camera head can be supported by resting on the table.

Referring to FIG. 5, one approach is shown here, in which the gamma camera weight rests on the table surface 513 and the gamma camera is aligned with the fenestrated breast paddle 51 using the fenestrations for alignment purposes. The exterior of the gamma camera head consists of external packaging 53 which has paddle alignment guides 52. Within the external packaging is the collimator 54, scintillator 55, detector 56 connected together using the normal epoxies and gels, and then the electronics 57 is suitably designed to receive and apply powering, control and data signals over the estimated 15 to 25 foot length of package external cable 510 that extends back towards the processing unit or filter panel of the MR room. The package internal cabling 58 and connectorization 59 connect the electronics 57 to the external cable 10. In this design, the control function is only for self test, status and calibration as required of the detector and electronics board. Also shown is the breast 511 which does not necessarily extend all the way down to the table top surface 513. The lower level of the upper body support is 512.

If a 10 cm×10 cm detection area is assumed, typical physical values for the various elements would have a collimator with a 1 mm hole diameter, a 0.16 mm septal thickness, and a 2 cm thickness. This would connect to a scintillator with 2 mm×2 mm pixellations. The 2×2 mm pixellations would be attached to a silicon photomultiplier (SiPM)-based detection system, available in the marketplace by SensL.

If the length of the fenestration is 5 mm, the paddle alignment guides will be slightly shorter, such as 3 or 4 mm, so that they don't interfere with the breast tissue that will protrude slightly into the opposite side of the fenestration. This design as shown is suitable for breast paddles that are vertically or near vertically oriented with respect to the table.

In this example, it is assume that the collimator is a straight-through hole variety, and that there is no requirement to align the external paddle fenestrations with the collimator openings. The breast paddle is assumed to be made of material that does not impact the gamma imaging performance.

In some instances, the breast paddles will be curved or non-vertical due to the pressure applied by the breast on the paddle. For curved paddles, an alignment guide can be made that will have a curved surface that matches the curvature of the breast paddle. For those cases where the breast paddle is non-vertical, the gamma camera head will still operate as long as the angle is not excessive. The exact angles of operation will depend on the details of the thickness of the gamma camera packaging. It is anticipated that padding and supports commonly used within interventional medical environments can be used to position the gamma camera head. Alternatively, simple wedges can be provided to allow different angles to be achieved.

Figure 6:
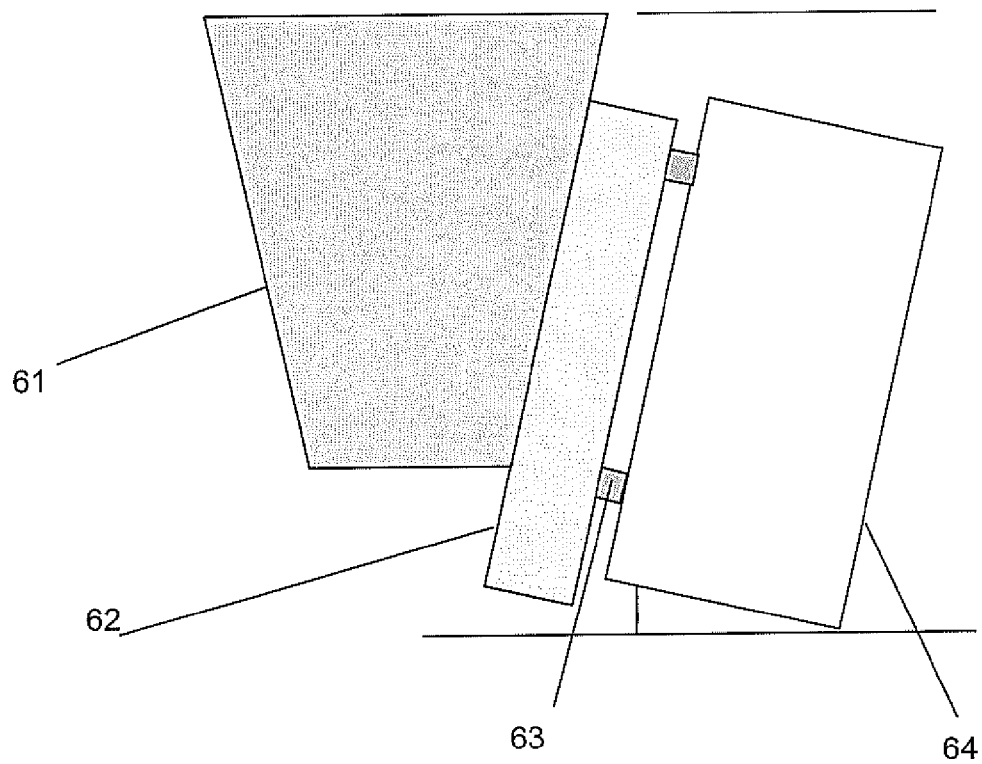
FIG. 6 shows a possible orientation of breast, breast paddle, and planar gamma camera head.

FIG. 6 shows a possible non-horizontal orientation of breast 61, breast paddle 62, and planar gamma camera head 64. A wedge can be inserted below the gamma camera system to ensure that it is supported and that it remains in the same position while imaging is occurring. The wedge can have simple lips and indentations that will assist in holding the gamma camera in position. Depending on the angles involved, the paddle alignment guides 63 may not be inserted into the same fenestration as they would if the angle was not quite so acute. It is the intention of this gamma camera head design to be able to retrofit to existing breast paddles that are commercially available and used in the medical community, and therefore there is nothing special about the particular fenestration shape that is used for insertion. The angles involved in the arrangement have been exaggerated to show the affect.

In all cases, it is assumed that a known fiducial based co-registration system is being used, and therefore the gamma camera head positioning by the fenestrations is strictly for general alignment and not for any specific co-registration alignment requirements. It is also evident that as shown, the gamma camera system may have a portion of the collimator unused, because the pendant breast may not extend far enough below the table to be imaged. It is possible to use padding and simple stands that are available in the medical intervention room to support the gamma camera weight in order to raise it so that as much of the breast as possible is imaged.

Figure 7:
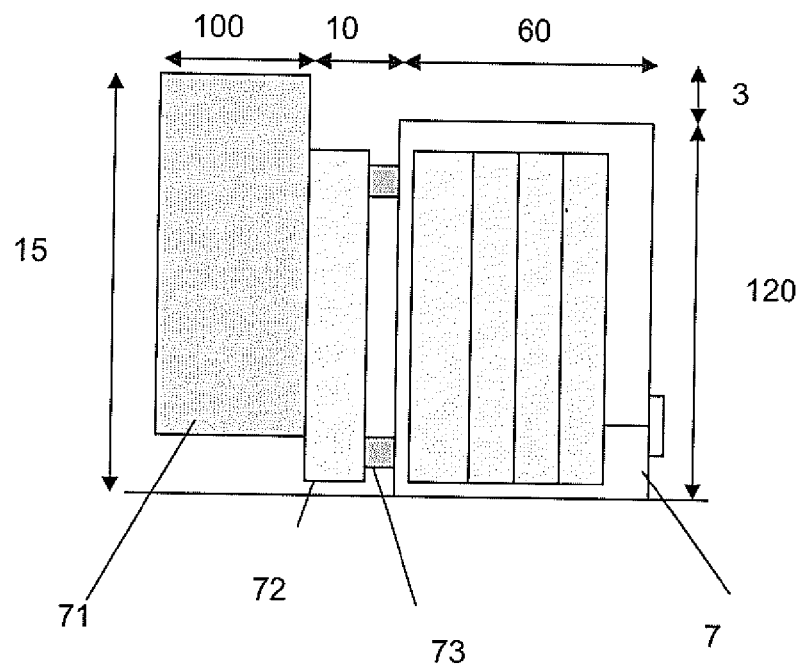
FIG. 7—Typical Dimensions for the Planar Gamma Camera Head and Breast Paddle.

FIG. 7 shows typical dimensions that might be reasonable for a typical patient. Average breast 71 diameters are assumed as 11 to 13 cm, and we assume that light compression brings the breast thickness in the direction between the paddles to 10 cm. By necessity, the breast volume is constant, so the breast diameter in the opposite direction will be increased to 12 to 14 cm, for example. The breast paddle 72 of thickness 5 mm is directly against the breast, and a gap of 5 mm is allowed between the edge of the gamma camera head 74 and the outer edge of the breast paddle 72, with alignment guides 73 providing alignment assistance. The gamma camera head thickness in this example is 60 mm, and it is anticipated that internal to the gamma camera head the collimator is 20 mm, the scintillator is 15 mm, and the detector and electronics, as well as some space for thermal management, cabling, and mechanical supports for the internal components, will use up the remaining 25 mm. The connector 75 is shown in the lower part of the package, high enough above the table to allow easy connectorization by a nurse's hand, but low enough so that the moment caused by any cable weight will not affect gamma camera head positioning.

Heating of the gamma camera elements will require airflow and venting of the internal systems. This can be done through openings in the case to allow air to flow through the system or through airflow management via the connectorization system. This connectorization option may require dedicated connectors for input and output airflow, distinct from the power, control and data connectorization. The difficulty with using air vents for the thermal management is both the potential for hot air to impact the patient as well as for the difficulty of maintaining shield requirements for the gamma camera. In the case where separate inflow and outflow air ventilation systems are needed, the outflow air will be vented on the upper part of the case.

There are breast paddle systems that do not use round or squarish fenestrations, but instead use horizontal guide systems. In this case, the alignment guides 73 will be different but the gamma camera head will not be different.

This particular design is best suited when the RF coils are not built into the breast paddles, but instead when the RF coils are built into the upper or lower surfaces of the upper body support or table. This is because in the general case, the gamma camera cannot image through an RF coil.

It is possible to image through the RF coil packaging if the particular location of the metal elements are known in advance within the coil. That is, some portions of the coil packaging are simply plastic in the cross-section, and do not contain materials that would alter the gamma camera performance. If these locations are known in advance, then it is possible to move the gamma camera into imaging position on the outside of the coil and image through the plastic, after which the gamma camera can be removed. This is difficult to know in a retrofit application however, so in general it is best to have openings and slots within the RF coil packaging design that ensure that no material is blocking and affecting the gamma camera performance.

Figure 8:
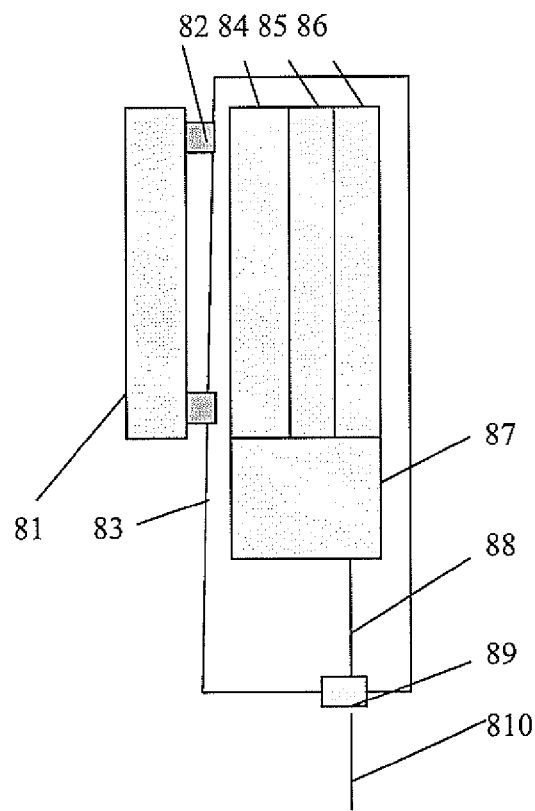
FIG. 8—An arrangement of the gamma camera head elements to allow a thinner version of the packaging.

FIG. 8 shows an alternative design approach for the planar gamma camera head. This system has the same internal elements and positioning and alignment methods as already discussed, with the exception that the cabling and connection between the detector 86 and electronics 87 needs to be modified. In this case, the electronics 87 are oriented to one side, allowing a thinner package depth to be obtained. This may be useful for some retrofit situations, and it will depend on the specific type of space and movement methods that are required.

Figure 9:
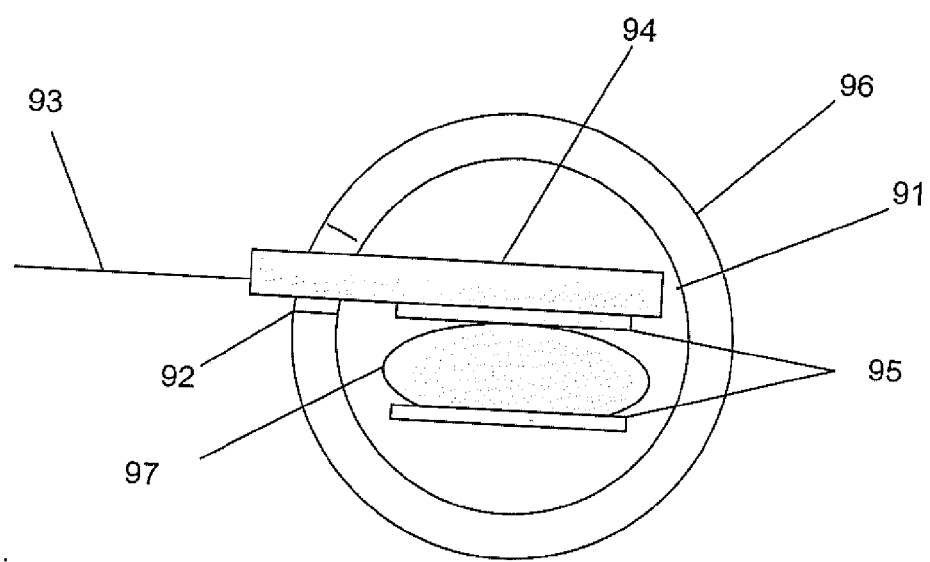
FIG. 9—Birdcage Breast coil design with planar gamma camera inserted.

One such situation that may be suitable for a thinner package is shown in FIG. 9, which shows a birdcage breast coil design from a top view. A breast 97 is gently held between two breast paddles 95. The gamma camera head 94 is inserted through a slot 92 of the birdcage coil. The thinner packaging design may be more useful, as the gamma camera head can be inserted through the slots of the birdcage design and is closer to the breast than the inner diameter of the birdcage coil 91 and the rear portion containing the electronics and connectorization can remain outside the RF coil and is potentially outside of the outer diameter of the birdcage coil 96. The interconnection cabling 93 extends from the rear of the gamma camera head. This design allows a relatively narrow slot to accommodate a collimator with a large face.

In all of these designs, the MRI imaging is done prior to be gamma imaging. This allows for an opportunity to use the MRI imaging session information to improve the gamma imaging session performance. In particular, MRI is known to be very sensitive, and so it can be expected that almost all potential lesions that might be cancerous can be imaged by the MRI system. Using this information, the particular positioning of the gamma camera collimator and scintillator can be improved.

Figure 10:
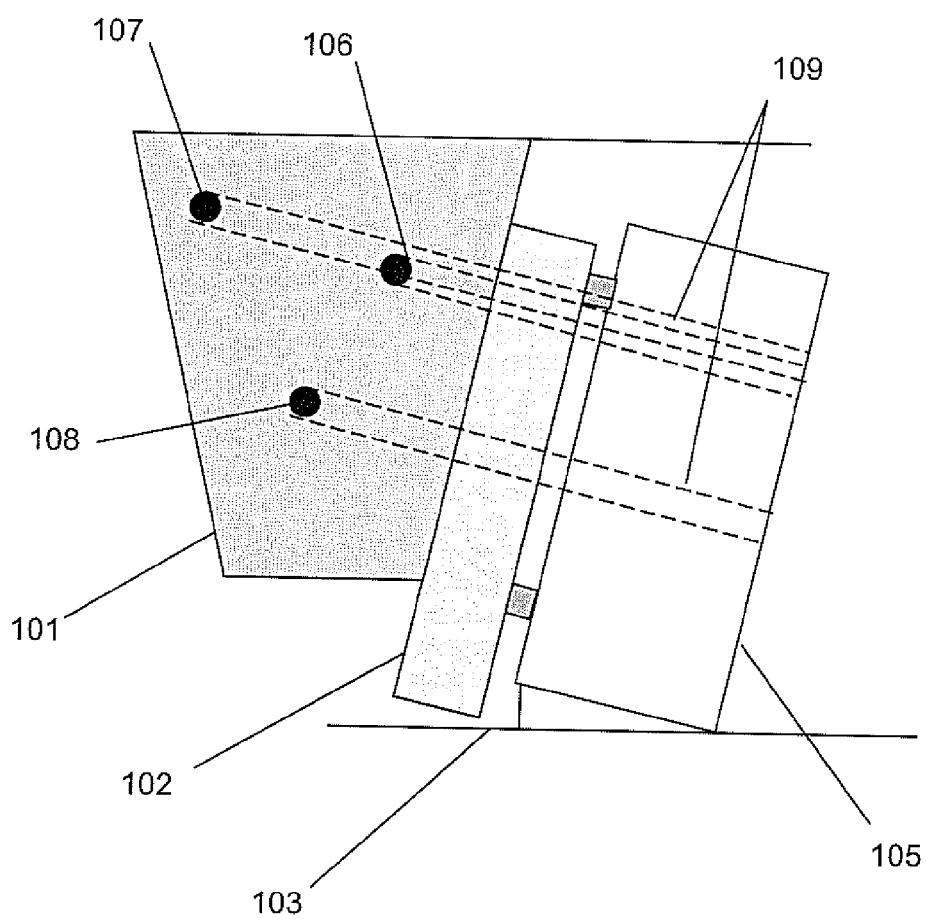
FIG. 10 shows a similar orientation of equipment in the case of a slab magnet.

FIG. 10 shows a planar gamma camera location which is not optimal for a parallel hole collimator. In this case, the MRI imaging result is assumed to be available within minutes after the MRI imaging session, and prior to the start of the gamma imaging session. The MRI results have indicated that there are three areas of interest that may contain cancerous lesions. These areas are lesion 1 106, lesion 2 107 and lesion 3 108. However, the gamma camera head 105, and hence the collimator within the gamma camera head, is oriented such that two of the lesion locations, lesion 106 and 107, line up and overlap, as shown by dotted lines 109 which approximate the route that the gamma photons emitted from lesion 106 and 107 will take through the parallel hole collimator. If both lesions have no uptake of radiotracer, then both lesions can be determined to not be of concern. If, however, either one or both of the lesions have radiotracer uptake, then it will be difficult or impossible to determine which of the lesions is emitting the photons. This predicament is only true if the parallel hole collimator, scintillator and detector are in a fixed position within the gamma camera head, and are not allowed to move.

Figure 11:
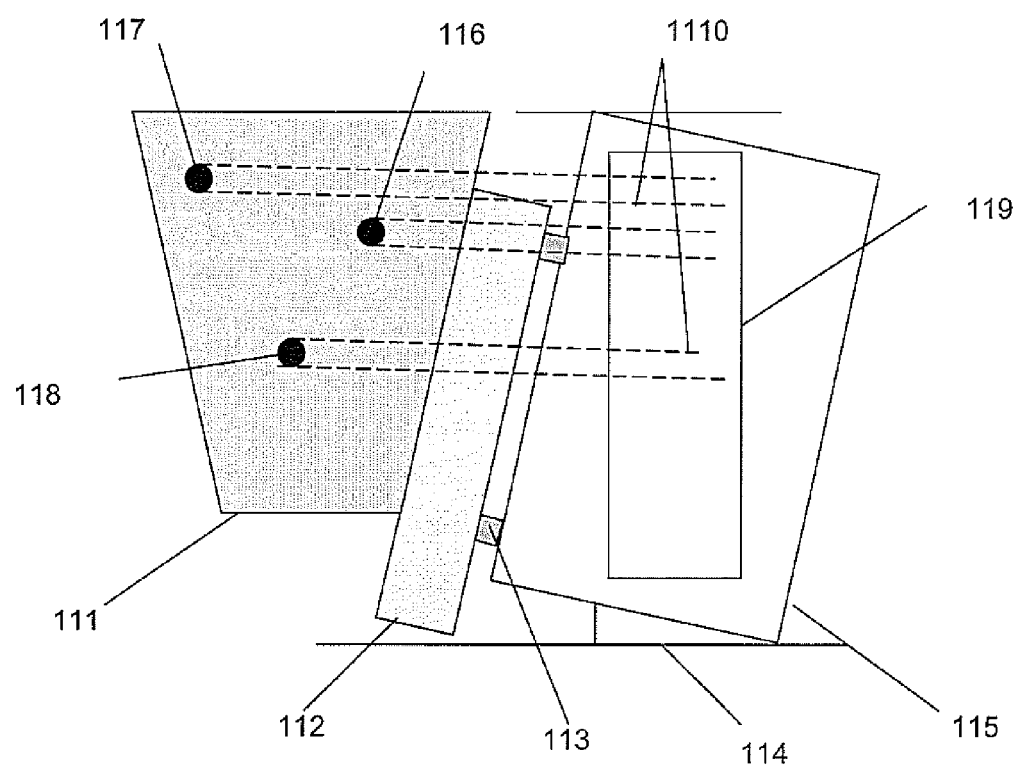
FIG. 11 illustrates a method of adjusting the orientation of the gamma camera so that the lesions are not shadowed or blocked by each other.

FIG. 11 shows a method of adjusting the orientation of the internal elements of the gamma camera head 119 so that the lesion's (lesion 1 116, lesion 2 117 and lesion 3 118) emissions do not overlap on the scintillator. The path that the photons will take through the parallel hole collimator are shown by dotted lines 1110. In this case, one has an improved ability to resolve which of the potential lesions may be of interest. In order to accommodate this approach, the external packaging of the gamma camera head 115 is larger than the collimator, scintillator and detector and an internal mechanical movement system is included that will allow movement of the internal elements. The internal elements that can be moved will include the collimator, scintillator and detector, and may also include the electronics system depending on whether a thinner or thicker gamma camera head design is used.

In addition, it is known however, that the gamma imaging session may uncover potential lesions within the breast region that have not been observed by the MRI imaging session. These potentially unknown lesion sites, however, typically would not deter the operator from optimally placing the gamma camera head, because it would be more useful to place the gamma head optimally for those lesions that are known at the time based on the MRI session information.

While the preferred embodiments of the invention have been described above, it will be recognized and understood that various modifications may be made therein, and the appended claims are intended to cover all such modifications which may fall within the spirit and scope of the invention.

The invention claimed is:

1. A method of imaging a breast comprising:
providing a patient lying on a table, said table having a raised platform with openings for the face and breasts of the patient;
providing a bore based or slab based magnetic resonance imaging (MRI) system having a radiofrequency (RF) coil, said RF coil having an opening therein, said MRI system generating a fringe field;
generating an MRI image of the breast of interest by placing the RF coil proximal to the breast of interest;
providing a magnetic resonance imaging (MRI) compatible gamma camera comprising:
an MRI-compatible gamma camera head arranged to be inserted through the opening in said RF coil;
a gamma shield; and
a processing system connected to the gamma camera head by cabling,
said gamma camera head being connected to an articulated arm and said gamma camera being located at a first position outside of the fringe field of the MRI system;
moving said articulated arm to move said gamma camera head from said first position to a second position wherein the gamma camera head is closer to the breast of interest than the inner diameter of the RF coil, said articulated arm moving from said first position to said second position by inserting the gamma camera head through the opening in the RF coil; and
generating a gamma image of the breast of interest with said gamma camera, characterized in that the magnetic resonance imaging and the gamma imaging are carried out sequentially and the patient is not moved or repositioned during either imaging process.

2. The method according to claim 1 wherein the gamma camera head comprises a collimator, a scintillator, a detector and an electronics assembly.

3. The method according to claim 1 wherein the gamma camera head is planar.

4. The method according to claim 1 wherein the gamma camera head is connected to an articulated arm for positioning the gamma camera head.

5. The method according to claim 1 further comprising a breast paddle for holding a patient's breast during imaging.

6. The method according to claim 5, wherein the gamma camera head includes alignment protrusions for aligning the gamma camera head onto the breast paddle.

7. The method according to claim 1 wherein the opening in the RF coil is a slot in the RF coil.

8. The method according to claim 1 wherein the opening in the RF coil is formed by removing a portion of the RF coil.

9. The method according to claim 1 wherein the opening in the RF coil is formed by deforming the RF coil.

10. The method according to claim 1 wherein the positioning of the gamma camera is determined by the results of the magnetic resonance imaging.

11. The method according to claim 1 wherein the magnetic resonance image and the gamma image are co-registered.

12. A pendant breast imaging system comprising:
a table for a patient to rest thereon, said table having a raised platform with openings for the face and breasts of the patient;
a bore based or slab based magnetic resonance imaging (MRI) system having a radiofrequency (RF) coil, said RF coil having an opening therein, said MRI system generating a fringe field; and a magnetic resonance imaging compatible gamma camera comprising:
- an MRI-compatible gamma camera head arranged to be inserted through the opening in said RF coil;
- a gamma shield; and
- a processing system connected to the gamma camera head by cabling, wherein said gamma camera head is connected to an articulating arm for moving said gamma camera head from a first position outside of the fringe field to a second position within the fringe field, wherein, during movement from said first position to said second position, the gamma camera head is inserted through the opening in said RF coil.

13. The pendant breast imaging system according to claim 12 wherein the gamma camera head comprises a collimator, a scintillator, a detector and an electronics assembly.

14. The pendant breast imaging system according to claim 12 wherein the gamma camera head is planar.

15. The pendant breast imaging system according to claim 12 further comprising a breast paddle for holding a patient's breast during imaging.

16. The pendant breast imaging system according to claim 15 wherein the gamma camera head includes alignment protrusions for aligning the gamma camera head onto the breast paddle.

17. The pendant breast imaging system according to claim 12 wherein the gamma camera head is arranged to be inserted through the opening in the RF coil such that the gamma camera head is closer to the patient than the inner diameter of the RF coil.

18. The pendant breast imaging system according to claim 17 wherein the opening in the RF coil is a slot in the RF coil.

19. The pendant breast imaging system according to claim 17 wherein the opening in the RF coil is formed by removing a portion of the RF coil.

20. The pendant breast imaging system according to claim 17 wherein the opening in the RF coil is formed by deforming the RF coil.

* * * * *